US011806067B2

(12) United States Patent
Dunning

(10) Patent No.: US 11,806,067 B2
(45) Date of Patent: *Nov. 7, 2023

(54) ADVANCED SIMULTANEOUS ACTIVATION ALGORITHM

(71) Applicant: Covidien LP, Mansfield, MA (US)

(72) Inventor: James E. Dunning, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/851,617

(22) Filed: Jun. 28, 2022

(65) Prior Publication Data

US 2022/0323137 A1   Oct. 13, 2022

Related U.S. Application Data

(63) Continuation of application No. 16/839,495, filed on Apr. 3, 2020, now Pat. No. 11,369,429, which is a (Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1233* (2013.01); *A61B 18/1482* (2013.01); (Continued)

(58) Field of Classification Search
CPC ............ A61B 18/1206; A61B 18/1233; A61B 18/1482; A61B 18/14; A61B 18/148; (Continued)

(56) References Cited

U.S. PATENT DOCUMENTS

D574,323 S   8/2008   Waaler
9,099,863 B2   8/2015   Smith et al.
(Continued)

FOREIGN PATENT DOCUMENTS

DE   179607 C   11/1906
DE   390937 C   3/1924
(Continued)

OTHER PUBLICATIONS

Wald et al., "Accidental Burns", JAMA, Aug. 16, 1971, vol. 217, No. 7, pp. 916-921.
(Continued)

*Primary Examiner* — Eun Hwa Kim
*Assistant Examiner* — C. C. P
(74) *Attorney, Agent, or Firm* — CARTER, DELUCA & FARRELL LLP

(57) ABSTRACT

An electrosurgical generator includes: a power supply configured to output a DC waveform; a power converter coupled to the power supply and configured to generate a radio frequency waveform based on the DC waveform; an active terminal coupled to the power converter and configured to couple to a first electrosurgical instrument and a second electrosurgical instrument; at least one sensor coupled to the power converter and configured to sense at least one property of the radio frequency waveform; and a controller coupled to the power converter. The controller is configured to: determine a first impedance associated with a first electrosurgical instrument and a second impedance associated with a second electrosurgical instrument based on the at least one property of the radio frequency waveform; and adjust at least one parameter of the radio frequency waveform based on the first impedance and the second impedance.

17 Claims, 5 Drawing Sheets

Related U.S. Application Data continuation of application No. 15/494,714, filed on Apr. 24, 2017, now Pat. No. 10,610,287.

(60) Provisional application No. 62/332,043, filed on May 5, 2016.

(51) Int. Cl.
 *A61B 18/00* (2006.01)
 *A61B 18/16* (2006.01)

(52) U.S. Cl.
 CPC ............. *A61B 18/14* (2013.01); *A61B 18/148* (2013.01); *A61B 18/16* (2013.01); *A61B 2018/0063* (2013.01); *A61B 2018/00577* (2013.01); *A61B 2018/00589* (2013.01); *A61B 2018/00601* (2013.01); *A61B 2018/00607* (2013.01); *A61B 2018/00648* (2013.01); *A61B 2018/00702* (2013.01); *A61B 2018/00779* (2013.01); *A61B 2018/00827* (2013.01); *A61B 2018/00845* (2013.01); *A61B 2018/00875* (2013.01); *A61B 2018/00892* (2013.01); *A61B 2018/126* (2013.01); *A61B 2018/1253* (2013.01); *A61B 2018/1266* (2013.01); *A61B 2018/1405* (2013.01)

(58) Field of Classification Search
 CPC .......... A61B 18/16; A61B 2018/00577; A61B 2018/00589; A61B 2018/00601; A61B 2018/00607; A61B 2018/0063; A61B 2018/00648; A61B 2018/00702; A61B 2018/00779; A61B 2018/00827; A61B 2018/00845; A61B 2018/00875; A61B 2018/00892; A61B 2018/1253; A61B 2018/126; A61B 2018/1266; A61B 2018/1405
 See application file for complete search history.

(56) References Cited

U.S. PATENT DOCUMENTS

| | | |
|---|---|---|
| 9,186,202 B2 | 11/2015 | Gilbert |
| 9,270,202 B2 | 2/2016 | Johnson et al. |
| 9,283,028 B2 | 3/2016 | Johnson |
| 2004/0097916 A1 | 5/2004 | Thompson et al. |
| 2004/0167508 A1 | 8/2004 | Wham et al. |
| 2010/0324548 A1* | 12/2010 | Godara ............. A61B 18/1492 606/34 |
| 2014/0232463 A1 | 8/2014 | Gilbert |
| 2014/0243815 A1 | 8/2014 | Kerr |
| 2014/0253140 A1 | 9/2014 | Gilbert |
| 2014/0254221 A1 | 9/2014 | Johnson et al. |
| 2014/0257270 A1 | 9/2014 | Behnke |
| 2014/0258800 A1 | 9/2014 | Gilbert |
| 2014/0276750 A1 | 9/2014 | Gilbert |
| 2014/0276753 A1 | 9/2014 | Wham et al. |
| 2014/0276754 A1 | 9/2014 | Gilbert et al. |
| 2014/0358138 A1 | 12/2014 | Mattmiller et al. |
| 2014/0376269 A1 | 12/2014 | Johnson et al. |
| 2015/0025521 A1 | 1/2015 | Friedrichs et al. |
| 2015/0025523 A1* | 1/2015 | Friedrichs .......... A61B 18/1206 606/34 |
| 2015/0032096 A1 | 1/2015 | Johnson |
| 2015/0032098 A1 | 1/2015 | Larson et al. |
| 2015/0032099 A1 | 1/2015 | Larson et al. |
| 2015/0032100 A1 | 1/2015 | Coulson et al. |
| 2015/0088116 A1 | 3/2015 | Wham |
| 2015/0088117 A1 | 3/2015 | Gilbert et al. |
| 2015/0088118 A1 | 3/2015 | Gilbert et al. |
| 2015/0088124 A1 | 3/2015 | Wham |
| 2015/0088125 A1 | 3/2015 | Wham |
| 2015/0119871 A1 | 4/2015 | Johnson et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2206473 | 7/2010 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| JP | 2005185657 A | 7/2005 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |

OTHER PUBLICATIONS

Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.

(56) References Cited

OTHER PUBLICATIONS

"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 11/242,458, filed Oct. 3, 2005 inventor: Becker.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
European Search Report dated Oct. 9, 2017 issued in corresponding EP Application No. 17169623.0.
European Search Report dated Aug. 15, 2018 issued in corresponding EP Appln. No. 17169623.0.

\* cited by examiner

ADVANCED SIMULTANEOUS ACTIVATION ALGORITHM

CROSS-REFERENCE TO RELATED APPLICATIONS

This application is a continuation of U.S. patent application Ser. No. 16/839,495, filed Apr. 3, 2020, now U.S. Pat. No. 11,369,429, which is a continuation of U.S. patent application Ser. No. 15/494,714, filed Apr. 24, 2017, now U.S. Pat. No. 10,610,287, which claims priority to and the benefit of U.S. Provisional Application No. 62/332,043 filed May 5, 2016. The disclosure of each of the foregoing applications are hereby incorporated by reference in its entirety herein.

BACKGROUND

Technical Field

The present disclosure relates to systems and methods for simultaneous activation of two or more electrosurgical instruments powered by a single electrosurgical generator. In particular, the present disclosure relates to an electrosurgical generator configured to prevent power surges during simultaneous activation and deactivation of multiple electrosurgical instruments.

Background of Related Art

Electrosurgery involves application of high radio frequency ("RF") electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

Some conventional electrosurgical generators allow for use of two or more electrosurgical instruments coupled to a single output rail of the electrosurgical generator. Thus, the electrosurgical generator splits the output from the single output rail to each of the instruments. This allows multiple surgeons to operate using a single generator. However, for a selected power setting, if both instruments were activated simultaneously, each of the instruments receives only a portion of the power, dependent on impedance of the tissue. Thus, if both instruments are operating simultaneously on the tissue having the same impedance, then each instrument only receives half of the selected power setting. In some instances, due to different impedances encountered by each of the electrosurgical instruments, some of the instruments may receive too much or too little power, as the conventional electrosurgical generators are incapable of calculating power output at each channel. Moreover, when the power flow to one of the instruments is deactivated, then the other instrument experiences a power surge as the electrosurgical generator supplies the full amount of power previously supplied to two instruments to a single instrument. Accordingly, there is a need for an electrosurgical generator configured to prevent power surges that occur during simultaneous deactivation of one of the multiple electrosurgical instruments.

SUMMARY

The present disclosure provides an electrosurgical generator including a non-resonant power converter having one or more switching elements controlled by a switching waveform (e.g., a pulse-width modulated waveform) generated by a controller. The generator also includes one or more sensors configures to measure voltage and current of the power output by the power converter. The electrosurgical generator includes an advanced simultaneous operational mode, during which the electrosurgical generator is set to a common power setting for two or more electrosurgical instruments coupled to a single output rail. While one of the electrosurgical instruments is used, e.g., a first electrosurgical instrument, the electrosurgical generator operates in a standard power control mode, during which the power is held constant within applicable impedance range and voltage and current limits. During this mode, impedance encountered by the first electrosurgical instrument is continuously calculated and averaged over a period of time, which may be from about 500 milliseconds ("ms") to about 1,000 ms. Once the second electrosurgical instrument is activated, simultaneously with the first electrosurgical instrument, the impedance encountered by the second electrosurgical instrument is in parallel with the impedance encountered by the first electrosurgical instrument, which results in a parallel impedance. At this point, the electrosurgical generator also calculates the total parallel impedance. Using the previously calculated first impedance and the total parallel impedance, the generator estimates and/or calculates the second impedance. The electrosurgical generator then adjusts the voltage supplied to one of the first or second electrosurgical instrument having the lower impedance to the selected power setting. The other electrosurgical instrument, the one having the higher impedance, receives higher power. Thus, the electrosurgical generator according to the present disclosure allows for simultaneous activation of multiple electrosurgical instruments based on measured impedance without drastic power changes.

According to one embodiment of the present disclosure, an electrosurgical generator is provided. The electrosurgical generator includes: a power supply configured to output a DC waveform; a power converter coupled to the power supply and configured to generate a radio frequency waveform based on the DC waveform; an active terminal coupled to the power converter and configured to couple to a first electrosurgical instrument and a second electrosurgical instrument; at least one sensor coupled to the power converter and configured to sense at least one property of the radio frequency waveform; and a controller coupled to the power converter. The controller is configured to: determine a first impedance associated with a first electrosurgical instrument and a second impedance associated with a second electrosurgical instrument based on the at least one property of the radio frequency waveform; and adjust at least one parameter of the radio frequency waveform based on the first impedance and the second impedance.

According to one aspect of the above embodiment, the electrosurgical generator also includes a user interface coupled to the controller, the user interface configured to receive a user input.

According to one aspect of the above embodiment, the controller is further configured to adjust the at least one parameter of the radio frequency waveform based on the user input.

According to one aspect of the above embodiment, the electrosurgical generator also includes a return terminal coupled to the power converter, wherein the return terminal is configured to couple to at least one return electrode pad. The active terminal is further configured to couple to a first monopolar electrosurgical instrument and a second monopolar electrosurgical instrument.

According to one aspect of the above embodiment, the at least one property is power.

According to one aspect of the above embodiment, the controller is further configured to adjust the power of the radio frequency waveform such that the power delivered to each of the first electrosurgical instrument and the second electrosurgical instrument is between 50% and 100% of the adjusted power.

According to another embodiment of the present disclosure, an electrosurgical system is disclosed. The electrosurgical system includes: a first electrosurgical instrument; a second electrosurgical instrument; and an electrosurgical generator. The electrosurgical generator includes a power supply configured to output a DC waveform; a power converter coupled to the power supply and configured to generate a radio frequency waveform based on the DC waveform; an active terminal coupled to the power converter and configured to couple to the first electrosurgical instrument and the second electrosurgical instrument; at least one sensor coupled to the power converter and configured to sense at least one property of the radio frequency waveform; and a controller coupled to the power converter. The controller configured to: determine a first impedance associated with the first electrosurgical instrument and a second impedance associated with the second electrosurgical instrument based on the at least one property of the radio frequency waveform; and adjust power of the radio frequency waveform based on the first impedance and the second impedance.

According to one aspect of the above embodiment, electrosurgical generator further includes a user interface coupled to the controller, the user interface is configured to receive a user input.

According to one aspect of the above embodiment, the controller is further configured to adjust the power of the radio frequency waveform based on the user input.

According to one aspect of the above embodiment, the electrosurgical generator further includes a return terminal coupled to the power converter, the return terminal is configured to couple to at least one return electrode pad.

According to one aspect of the above embodiment, the active terminal is further configured to couple to a first monopolar electrosurgical instrument and a second monopolar electrosurgical instrument.

According to one aspect of the above embodiment, the first electrosurgical instrument is activated prior to the second electrosurgical instrument.

According to one aspect of the above embodiment, the at least one sensor is configured to measure the first impedance prior to activation of the second electrosurgical instrument.

According to one aspect of the above embodiment, the at least one sensor is configured to measure total impedance after activation of the first electrosurgical instrument and the second electrosurgical instrument.

According to one aspect of the above embodiment, the controller is configured to determine the second impedance based on the total impedance and the first impedance.

According to one aspect of the above embodiment, the controller is further configured to adjust the power such that the power delivered to one of the first electrosurgical instrument or the second electrosurgical instrument having a lower impedance does not exceed the adjusted power.

According to one aspect of the above embodiment, the controller further configured to adjust the power such that the power delivered to one of the first electrosurgical instrument or the second electrosurgical instrument having a higher impedance is more than half of the adjusted power.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with any electrosurgical instrument. It should also be appreciated that different electrical and mechanical connections and other considerations may apply to each particular type of instrument.

Briefly, an electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various electrosurgical instruments (e.g., monopolar instruments, return electrode pads, bipolar electrosurgical forceps, footswitches, etc.). Further, the generator includes electronic circuitry configured to generate radio frequency energy specifically suited for powering electrosurgical instruments operating in various electrosurgical modes (e.g., cut, blend, coagulate, division with hemostasis, fulgurate, spray, etc.) and procedures (e.g., monopolar, bipolar, vessel sealing).

Figure 1:
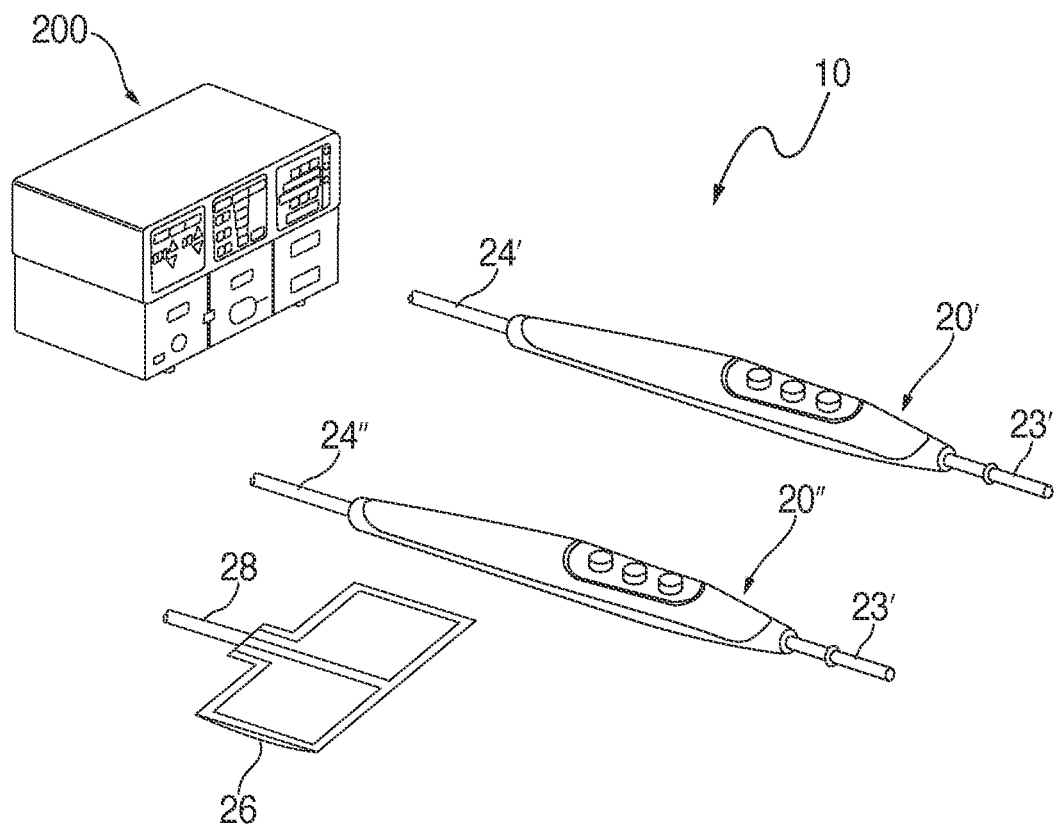
FIG. 1 is a perspective view of an electrosurgical system according to an embodiment of the present disclosure.

Referring to FIG. 1 an electrosurgical system 10 is shown which includes one or more monopolar electrosurgical instruments 20' and 20" having one or more active electrodes 23' and 23" (e.g., electrosurgical cutting probe, ablation electrode(s), etc.) for treating tissue of a patient. Electrosurgical alternating RF current is supplied to the instruments 20' and 20" by a generator 200 via supply lines 24' and 24", respectively, that are connected to an active terminal 230 (FIG. 3) of the generator 200, allowing the instruments 20' and 20" to cut, coagulate, and/or otherwise treat tissue. The alternating RF current is returned to the generator 200 through a return electrode pad 26 via a return line 28 at a return terminal 232 (FIG. 3) of the generator 200. The system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween. In embodiments, the system 10 may also include one or more bipolar electrosurgical instruments, for example, a bipolar electrosurgical forceps (not shown), having one or more electrodes for treating tissue of a patient. In further embodiments, the generator 200 according to the present disclosure may also be configured to simultaneously activate bipolar electrosurgical instruments in a manner described below.

Figure 2:
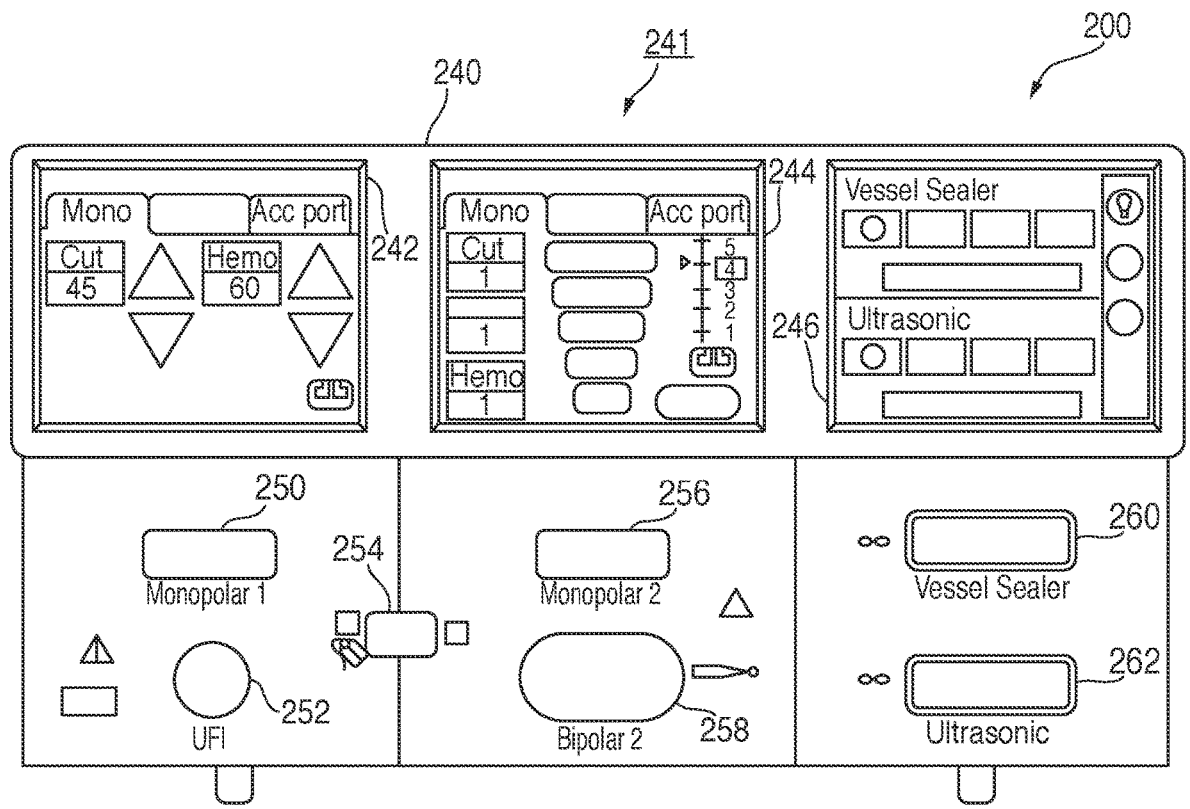
FIG. 2 is a front view of an electrosurgical generator of the electrosurgical system of FIG. 1 according to an embodiment of the present disclosure.

With reference to FIG. 2, a front face 240 of the generator 200 is shown. The generator 200 may include a plurality of ports 250-262 to accommodate various types of electrosurgical instruments. The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., more monopolar electrosurgical instruments 20' and 20", electrosurgical forceps, etc.). The user then adjusts inputs by simply touching corresponding menu options.

Screen 242 controls monopolar output and the instruments connected to the ports 250 and 252. Port 250 is configured to couple to a monopolar electrosurgical instrument (e.g., electrosurgical instruments 20' and 20") and port 252 is configured to couple to a foot switch (not shown). The foot switch may be used to provide for additional inputs (e.g., replicating inputs of the generator 200). Screen 244 controls monopolar and bipolar output and the instruments connected to the ports 256 and 258. Port 256 is configured to couple to other monopolar instruments. Port 258 is configured to couple to a bipolar instrument (not shown).

Screen 246 controls the electrosurgical forceps that may be plugged into one of the ports 260 and 262, respectively. The generator 200 outputs energy through the ports 260 and 262 suitable for sealing tissue grasped by the electrosurgical forceps. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The active and return terminals 230 and 232 (FIG. 3) may be coupled to any of the desired ports 250-262. In embodiments, the active and return terminals 230 and 232 may be coupled to the ports 250-262.

Figure 3:
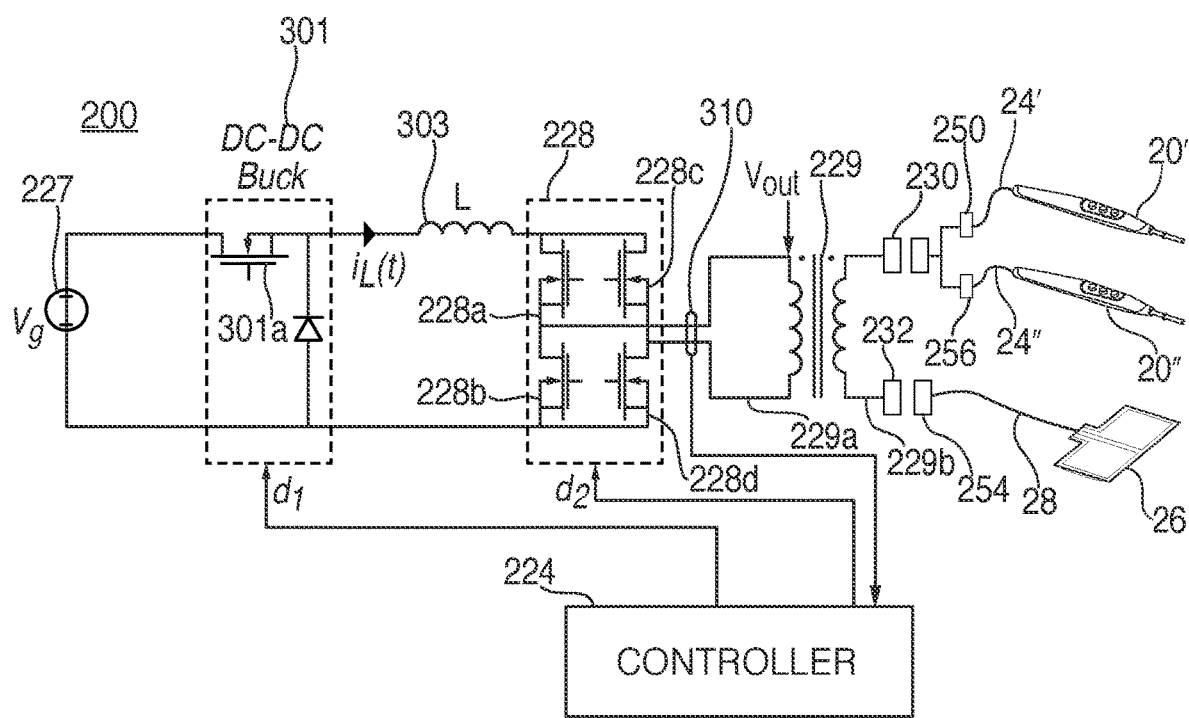
FIG. 3 is a schematic diagram of the electrosurgical system of FIG. 1 according to an embodiment of the present disclosure.

With reference to FIG. 3, the generator 200 includes a controller 224, a power supply 227, and a power converter 228. The power supply 227 may be a high voltage, DC power supply connected to an AC source (e.g., line voltage) and provides high voltage, DC power to the power converter 228, which then converts high voltage, DC power into RF energy and delivers the energy to the active terminal 230. The energy is returned thereto via the return terminal 232. In particular, electrosurgical energy for energizing the monopolar electrosurgical instruments 20' and 20" coupled to ports 250 and 256 is delivered through the active terminal 230 and returned through the return electrode pad 26 coupled to the port 254, which in turn, is coupled to the return terminal 232. The active and return terminals 230 and 232 are coupled to the power converter 228 through an isolation transformer 229. The isolation transformer 229 includes a primary winding 229a coupled to the power converter and a secondary winding 229b coupled to the active and return terminals 230 and 232.

The generator 200 also includes a DC-DC buck converter 301 coupled to the power supply 227. Furthermore, an inductor 303 is electrically coupled to the DC-DC buck converter 301 and the power converter 228. The inductor 303 may have a relatively large inductance which smoothes the current supplied to the power converter 228, such that the inductor 303 is configured to supply relatively constant current to the power converter 228. The output of power converter 228 transmits current through an isolation transformer 229 to the load e.g., tissue being treated.

The power converter 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 228 may be a resonant RF amplifier or a non-resonant RF amplifier, as shown. A non-resonant RF amplifier, as used herein, denotes an amplifier lacking any tuning components, i.e., conductors, capacitors, etc., disposed between the power converter and the load, e.g., tissue.

The controller 224 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 224 includes an output port that is operably connected to the power supply 227 and/or power converter 228 allowing the processor to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or power converter 228, which adjusts the DC and/or power supply, respectively.

The generator 200 according to the present disclosure may also include a plurality of sensors 310. In the embodiment illustrated in FIG. 3, the sensors 310 are coupled to a rail 305, which couples the power converter 228 to the primary winding 229a of the transformer 229. Thus, the sensors 310 are configured to sense voltage, current, and other electrical properties of energy supplied to the active and return terminals 230 and 232 through the rail 305.

In further embodiments, the sensors 310 may be coupled to the power supply 227, DC-DC buck converter 301, and/or the inductor 303, and may be configured to sense properties of DC current supplied to the power converter 228. The controller 224 also receives input signals from the input controls of the generator 200 and/or the instruments 20' and 20", and/or electrosurgical forceps 30. The controller 224 utilizes the input signals to adjust power outputted by the generator 200 and/or performs other control functions thereon.

The DC-DC buck converter 301 includes a switching element 301a and power converter 228 includes a plurality of switching elements 228a-228d arranged in an H-bridge topology. In embodiments, power converter 228 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicone carbide, or any other suitable wide bandgap materials.

The controller 224 is in communication with both DC-DC buck converter 301 and power converter 228, in particular, the switching elements 301a and 228a-228d, respectively. Controller 224 is configured to output control signals, which may be a pulse-width modulated ("PWM") signal, to switching elements 301a and 228a-228d. In particular, controller 224 is configured to modulate a control signal $d_1$ supplied to switching element 301a of DC-DC buck converter 301 and control signal $d_2$ supplied to switching elements 228a-228d of power converter 228. Additionally, controller 224 is configured to calculate power characteristics of generator 200, and control generator 200 based at least in part on the measured power characteristics including, but not limited to, current passing through the inductor 303, DC output of the DC-DC buck converter 301, and the voltage and current at the output of power converter 228.

Figure 4:
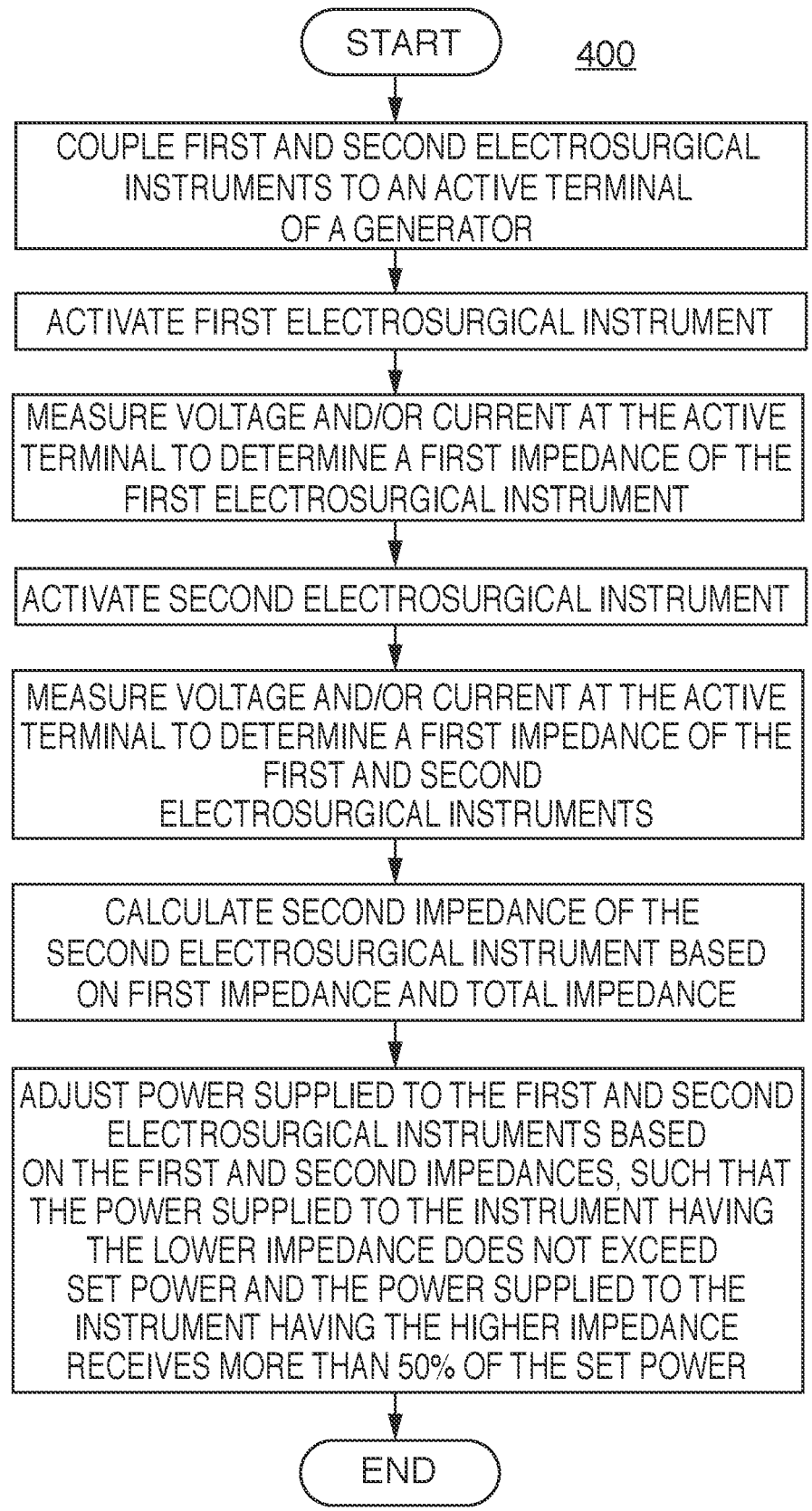
FIG. 4 is a flow chart of a method for controlling the electrosurgical generator FIG. 2 according to an embodiment of the present disclosure.

With reference to FIG. 4, a method 400 according to the present disclosure for controlling the generator 200 during simultaneous activation of electrosurgical instruments 20' and 20" is described. Method 400 is also described below concurrently with FIG. 5, which shows a combined plot of impedance encountered by each of the electrosurgical instruments 20' and 20" and power delivered thereto.

Figure 5:
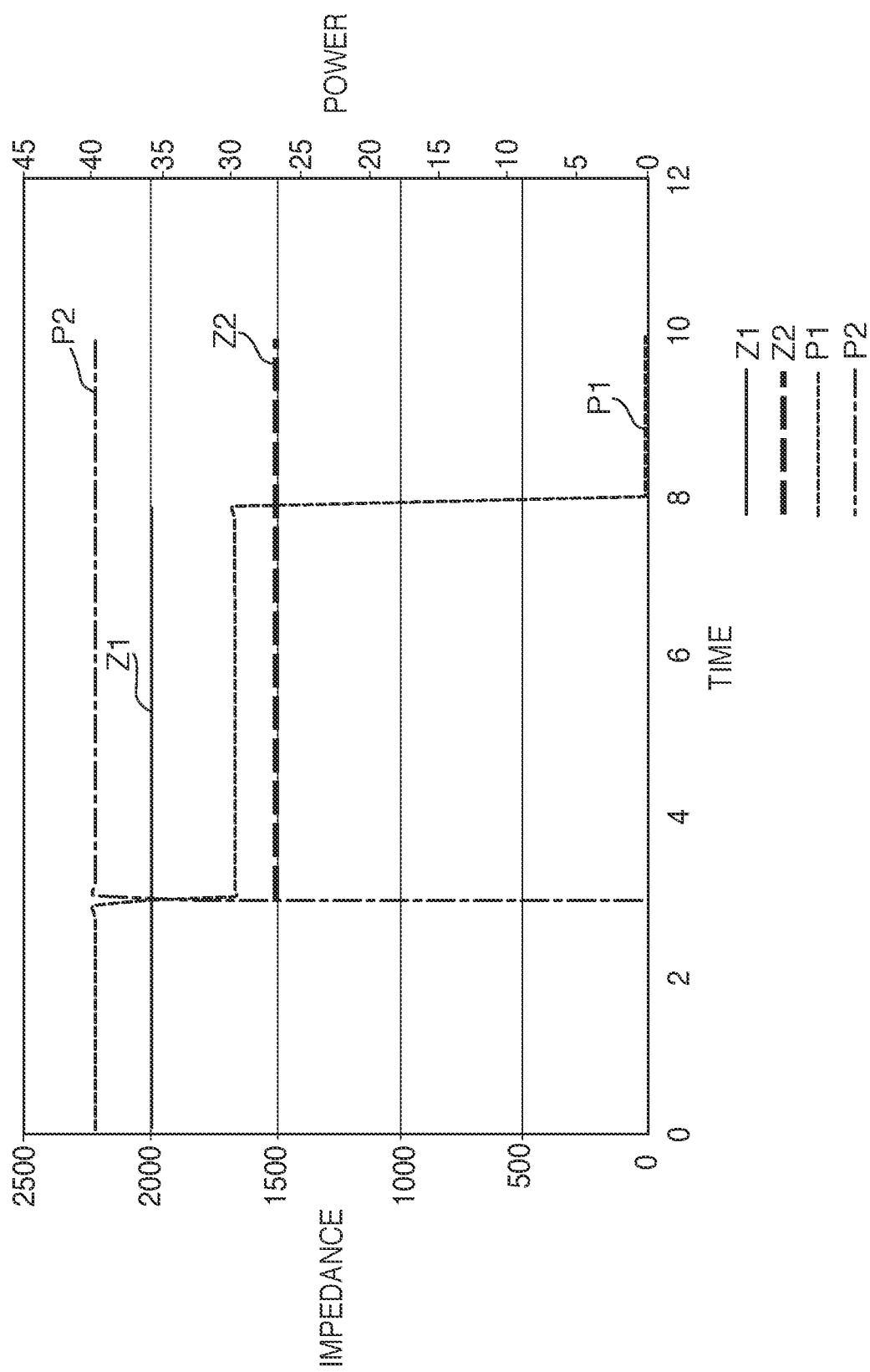
FIG. 5 is an impedance and power plot for simultaneously activating two electrosurgical instruments according to an embodiment of the present disclosure.

Initially, the electrosurgical instruments 20' and 20" are coupled to the active terminal 230 of the generator 200 through the ports 250 and 256. The user may select a desired electrosurgical mode (e.g., cut, blend, coagulate, division with hemostasis, fulgurate, spray, etc.). The user also selects the power/intensity setting at which the electrosurgical instrument 20' is operated through the user interface 241. Thereafter, the electrosurgical instrument 20' is activated by signaling the generator 200 to supply electrical power. In response, electrosurgical energy is supplied to the electrosurgical instrument 20', during which the sensors 310 continually monitor electrical properties of the supplied energy, such as voltage and current. The monitored voltage and current values are supplied to the controller 224, which calculates the impedance encountered by the electrosurgical instrument 20' during treatment. In embodiments, the controller 224 may continuously calculate impedance based on the measured voltage and current values to obtain first instrument impedance Z1 (e.g., impedance of the electrosurgical instrument 20') as shown in FIG. 5. The calculated impedance may be averaged to provide a moving average over a defined time period. The time period for the moving impedance average may be from about 100 milliseconds (ms) to about 2,000 ms, in embodiments, the time period may be from about 500 ms to about 1,000 ms.

The second electrosurgical instrument 20" may be activated simultaneously with or after the first electrosurgical instrument 20'. As the second electrosurgical instrument 20" contacts tissue, the tissue impedance encountered by the second electrosurgical instrument 20", Z2, is in parallel with impedance Z1 of the first electrosurgical instrument 20'. As described above, the sensors 310 measure voltage and current through the rail 305, which supplies energy to the active terminal 230, to which both of the first and second electrosurgical instrument 20' and 20" are coupled. Accordingly, the sensors 310 are capable of determining voltage and current for the combined power supplied to the first and second electrosurgical instruments 20' and 20". The controller 224 calculates the total impedance, Ztotal, based on the total measured voltage and current. The Ztotal value is based on the parallel combination of Z1 and Z2. Accordingly, the controller 224 is configured to calculate Z2, which cannot be measured directly by the sensors 310 as the first and second electrosurgical instruments 20' and 20" share a common output, namely the active terminal 230 through the rail 305. In particular, the controller 224 is configured to calculate Z2 based on the following formulas (I) and (II):

$$Z\text{total} = Z1 * Z2 / (Z1 + Z2) \tag{I}$$

$$Z2 = Z1 * Z\text{total} / (Z1 - Z\text{total}) \tag{II}$$

In formulas (I) and (II), Z1 is the impedance calculated based on measured voltage and current when only one electrosurgical instrument (e.g., first electrosurgical instrument 20') is activated, Ztotal is the impedance calculated based on measured voltage and current when both electrosurgical instruments 20' and 20" are activated, and Z2 is the impedance encountered by the second electrosurgical instrument 20".

Once the controller 224 calculates Z2, both Z1 and Z2 are known, the controller 224 adjusts the power output of the power converter 228 based on the selected power setting and the impedance of both of the electrosurgical instruments 20' and 20". In particular, the controller 224 adjusts the power to provide for a change in impedance due to addition of the impedance encountered by the second electrosurgical instrument 20". However, power is adjusted not to exceed the initial power setting and to ensure that the electrosurgical instrument with the lower impedance receives the power at the initial power setting. The power is also adjusted such that the other electrosurgical instrument receives more than half of the selected power setting.

The power and impedance plots for each of the electrosurgical instruments 20' and 20" are described in further detail below with respect to FIG. 5. In particular, plots P1 and Z1 illustrate exemplary power delivered to and the measured impedance encountered by the first electrosurgical instrument 20', respectively. The electrosurgical instrument 20' is activated at the selected power setting of about 40 watts and the impedance is constant at about 2,000 ohms. At about 3 seconds, the second electrosurgical instrument 20" is activated and the controller 224 determines that the impedance of the second electrosurgical instrument 20" is about 1,500 ohms, based on the total impedance, Ztotal. Since the addition of another electrosurgical instrument in parallel results in decrease in impedance, the controller 224 signals the power converter to adjust its output such that the second electrosurgical instrument 20", which has the lower impedance, receives the power at the selected setting of about 40 watts. Based on that setting, the first electrosurgical instrument 20' receives about 30 watts, which is larger than 50% of the initial setting of 40 watts. This calculation and adjustment in power prevents large swings in power, such that when the first electrosurgical instrument 20' is deactivated at about 8 seconds, the second electrosurgical instrument 20" continues to receive power at the initial power setting of about 40 watts, rather than receiving the higher combined power for both of the electrosurgical instruments 20' and 20".

In embodiments, the generator 200 may include individual rails for each of the ports 250 and 256 and the sensors 310 may be coupled to each of the rails to monitor current and voltage therein. The controller 224 may then calculate power for each rail individually and signal the power converter 228 to adjust the power dynamically to match the set power on each of the rail as described above with respect to the embodiment of FIG. 3. In particular, the controller 224 signals the power converter 228 to adjust the power dynamically at the rail having the highest current not to exceed the power setting.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator comprising:
   an active terminal configured to couple to a first electrosurgical instrument and a second electrosurgical instrument;
   a power converter coupled to the active terminal and configured to supply a radio frequency waveform simultaneously to the first electrosurgical instrument and the second electrosurgical instrument;
   a sensor coupled to the power converter and configured to sense at least one property of the radio frequency waveform; and
   a controller coupled to the power converter, the controller configured to:
      determine a first impedance associated with the first electrosurgical instrument;
      determine a total impedance of the first and second electrosurgical instruments;
      determine a second impedance associated with the second electrosurgical instrument based on the total impedance and the first impedance; and
      adjust at least one parameter of the radio frequency waveform based on the first impedance and the second impedance.

2. The electrosurgical generator according to claim 1, further comprising:
   a user interface coupled to the controller, the user interface configured to receive a user input.

3. The electrosurgical generator according to claim 2, wherein the controller is further configured to adjust the at least one parameter of the radio frequency waveform based on the user input.

4. The electrosurgical generator according to claim 1, further comprising a return terminal coupled to the power converter, wherein the return terminal is configured to couple to at least one return electrode pad.

5. The electrosurgical generator according to claim 4, wherein the active terminal is further configured to couple to a first monopolar electrosurgical instrument and a second monopolar electrosurgical instrument.

6. The electrosurgical generator according to claim 1, wherein the controller is further configured to adjust the power of the radio frequency waveform such that the power delivered to each of a first electrosurgical instrument and a second electrosurgical instrument is between 50% and 100% of the adjusted power.

7. An electrosurgical system comprising:
   a first electrosurgical instrument;
   a second electrosurgical instrument; and
   an electrosurgical generator including a power converter configured to supply a radio frequency waveform simultaneously to the first electrosurgical instrument and the second electrosurgical instrument;
      a sensor coupled to the power converter and configured to sense at least one property of the radio frequency waveform; and
      a controller coupled to the power converter, the controller configured to:
         determine a first impedance associated with the first electrosurgical instrument;
         determine a total impedance of the first and second electrosurgical instruments;
         determine a second impedance associated with the second electrosurgical instrument based on the total impedance and the first impedance; and
         adjust power of the radio frequency waveform based on the first impedance and the second impedance.

8. The electrosurgical system according to claim 7, wherein the electrosurgical generator further includes a user interface coupled to the controller, the user interface is configured to receive a user input.

9. The electrosurgical system according to claim 8, wherein the controller is further configured to adjust the power of the radio frequency waveform based on the user input.

10. The electrosurgical system according to claim 7, wherein the electrosurgical generator further includes a return terminal coupled to the power converter, the return terminal is configured to couple to at least one return electrode pad.

11. The electrosurgical system according to claim 10, wherein the first and second electrosurgical instruments are monopolar electrosurgical instruments.

12. The electrosurgical system according to claim 7, wherein the controller is configured to activate the first electrosurgical instrument prior to the second electrosurgical instrument.

13. The electrosurgical system according to claim 12, wherein the sensor is configured to measure the first impedance prior to activation of the second electrosurgical instrument.

14. The electrosurgical system according to claim 7, wherein the sensor is configured to measure the total impedance after activation of the first electrosurgical instrument and the second electrosurgical instrument.

15. The electrosurgical system according to claim 7, wherein the controller is further configured to determine which electrosurgical instrument of the first or second electrosurgical instruments has a lower impedance and adjust the power such that the power delivered to the electrosurgical instrument having the lower impedance does not exceed the adjusted power.

16. The electrosurgical system according to claim 7, wherein the controller is further configured to determine which electrosurgical instrument of the first or second electrosurgical instruments has a higher impedance value and adjust the power such that the power delivered to the electrosurgical instrument having the higher impedance is more than half of the adjusted power.

17. A method for simultaneous activation of two or more electrosurgical instruments, the method comprising:
  supplying a radio frequency waveform from a power converter of an electrosurgical generator simultaneously to a first electrosurgical instrument and a second electrosurgical instrument;
  sensing at least one property of the radio frequency waveform through at least one sensor coupled to the power converter;
  determining a first impedance associated with the first electrosurgical instrument;
  determining a total impedance of the first and second electrosurgical instruments;
  determine a second impedance associated with the second electrosurgical instrument based on the total impedance and the first impedance; and
  adjusting power of the radio frequency waveform based on the first impedance and the second impedance.

* * * * *